United States Patent [19]

Kerr et al.

[11] Patent Number: 4,876,721

[45] Date of Patent: Oct. 24, 1989

[54] METHOD AND DEVICE FOR IDENTIFYING DIFFERENT SPECIES OF HONEYBEES

[75] Inventors: Howard T. Kerr, Maryville; Michael E. Buchanan, Lenoir City; Kenneth H. Valentine, Knoxville, all of Tenn.

[73] Assignee: Martin Marietta Energy Systems, Inc., Oak Ridge, Tenn.

[21] Appl. No.: 163,673

[22] Filed: Mar. 3, 1988

[51] Int. Cl.$^4$ ............................................. H04R 29/00
[52] U.S. Cl. ........................................................ 358/56
[58] Field of Search .................. 381/56; 324/160, 166, 324/178

[56] References Cited

U.S. PATENT DOCUMENTS 4,118,601 10/1978 Yeap ...................................... 381/56

FOREIGN PATENT DOCUMENTS 739067 5/1955 United Kingdom .

OTHER PUBLICATIONS

E. F. Woods, "Electronic Prediction of Swarming in Bees," NATURE, Sep. 19, 1959, vol. 184, pp. 842-844.
Jacob S. Ishay, "The Sounds of Honeybees and Social Wasps are Always Composed of a Uniform Frequency," Journal Acoustical Society of America, 72(3), Sep. 1982, pp. 671-675.
N. P. Goyal et al., "Wing Beat Frequencies of Apis Cerana Indica and Apis Mellifera," Journal of Apicultural Research 16(1): 47-48 (1977).
W. F. Towne, "Acoustic and Visual Cues in the Dances of Four Honeybee Species," Behavioral Ecology and Sociobiology (1985) 16:185-187, vol. 16, No. 2, pp. 185-187.
A. Michelsen et al., "Sound and Vibrational Signals in the Dance Language of the Honeybee," Behavioral Ecology and Sociobiology, vol. 18, No. 3, 1986, pp. 207-212.
S. S. Schneider et al., "Quacking": A Sound Produced by Worker Honeybees After Exposure to Carbon Dioxide, Journal of Apicultural Research 23(1), 1984, pp. 25-30.
E. K. Es'kov, "Encoding of Target Distance Information by Honeybees," Problems of Information Transmission, vol. 8, No. 2, 1972, pp. 146-150.
D. M. Unwin et al., "Wingbeat Frequency, Temperature and Body Size in Bees and Flies," Physiological Entomolgy, (1984) 9, pp. 115-121.
S. Fuchs et al., "The Sound Production, A Means of Defense for the Honeybee Colony," Apidologie, 1974; vol. 5, pp. 271-287.
D. G. Dietlein, "A Method for Remote Monitoring of Activity of Honeybee Colonies by Sound Analysis," Journal of Apicultural Research, vol. 24, No. 3, (1985), pp. 176-183.

Primary Examiner—Tommy P. Chin
Attorney, Agent, or Firm—James M. Spicer; Bruce M. Winchell

[57] ABSTRACT

A method and device have been provided for distinguishing Africanized honeybees from European honeybees. The method is based on the discovery of a distinct difference in the acoustical signatures of these two species of honeybees in flight. The European honeybee signature has a fundamental power peak in the 210 to 240 Hz range while the Africanized honeybee signature has a fundamental power peak in the 260 to 290 Hz range. The acoustic signal produced by honeybees is analyzed by means of a detecting device to quickly determine the honeybee species through the detection of the presence of frequencies in one of these distinct ranges. The device includes a microphone for acoustical signal detection which feeds the detected signal into a frequency analyzer which is designed to detect the presence of either of the known fundamental wingbeat frequencies unique to the acoustical signatures of these species as an indication of the identity of the species and indicate the species identity on a readout device.

13 Claims, 4 Drawing Sheets

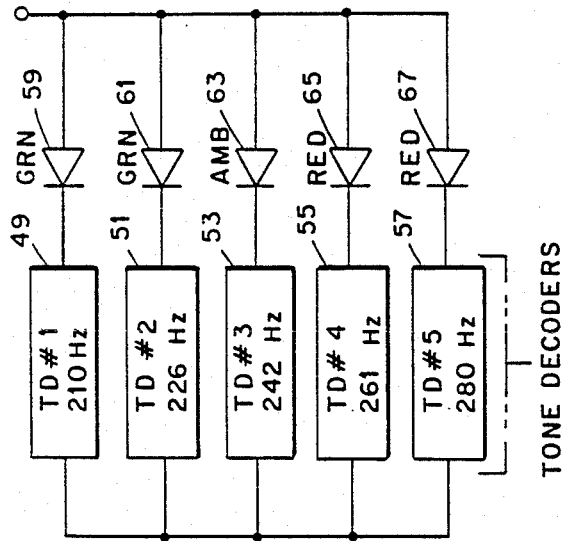
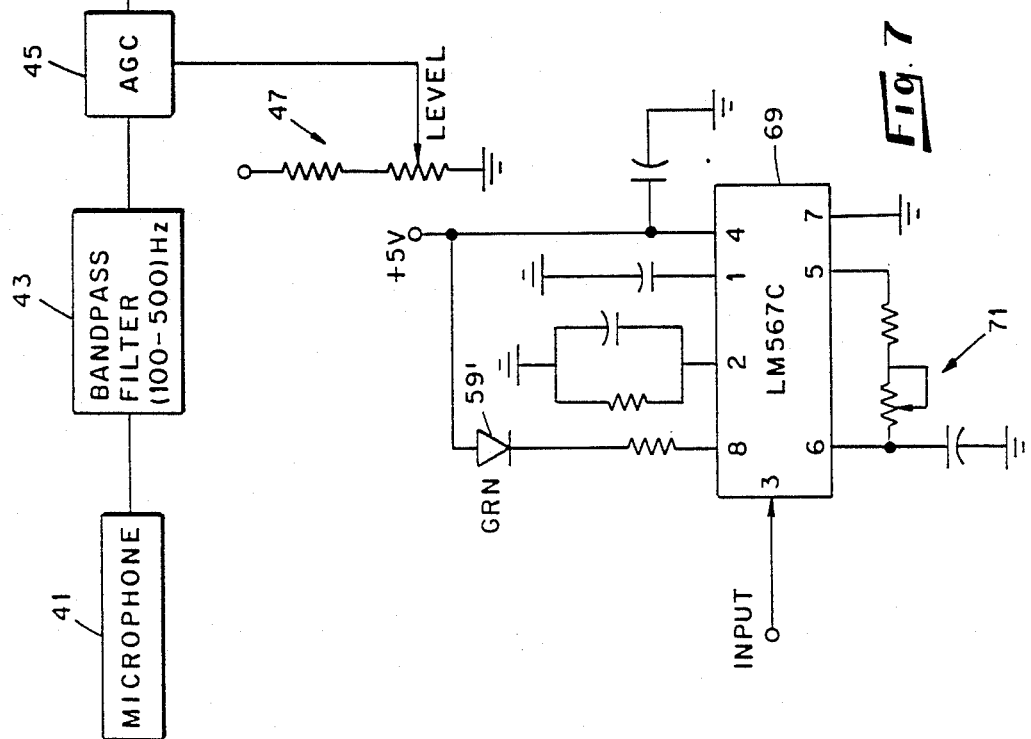

METHOD AND DEVICE FOR IDENTIFYING DIFFERENT SPECIES OF HONEYBEES

BACKGROUND OF THE INVENTION

This invention, which is a result of a contract with the United States Department of Energy, relates generally to acoustical signature based identification methods and devices and, more specifically, to methods and devices for the identification of different species of honeybees.

Several species of the family Apis Mellifera (AM) (honey producers), commonly referred to as honeybees, exist throughout the world and some species are so similar that positive identification requires sophisticated taxonomical procedures. A specific case of great importance to North America involves the identification of Apis Mellifera Scutellata, referred to herein as Africanized honeybees, Apis Mellifera Mellifera, referred to herein as European honeybees, and genetic crosses of these two species. The Africanized honeybees were introduced into South America about 30 years ago. Progenies of these bees have migrated toward North America at a rate of about 200–300 miles per year and are now being found in portions of Mexico. The extremly strong nest defensive behavior of the Africanized bees, often referred to as "killer" bees, relative to the existing population of European honeybees in the United States poses a major public health problem and will seriously impact agricultural productivity in that their presence will radically alter pollination of U.S. crops valued at more than $20 billion annually and a variety of wild flowers that have important ecological roles. Efficient control of honeybee populations in the United States by beekeepers and regulatory officials will be required to minimize the threats of the Africanized species while preserving European species now used for pollination and honey production.

If present migration rates continue, these Africanized honeybees will invade the United States before 1990. Although these bees are no more venomous than the European honeybees, they are much more responsive to disturbance of their nest, more likely to sting, and pursue their victims for much greater distances. They also swarm much more often than European honeybees and invade hives occupied by European bees. Thus, beekeepers will have to move hives out away from populated areas and provide proper safety for the general public to continue to keep honeybees if the invasion is not controlled.

Prior to applicants' present invention, there were no known techniques for immediate field identification of honeybees. Existing identification techniques involve sophisticated laboratory equipment and skilled analysts., the methods are very time consuming and not suitable for field surveillance. One known system is the Fast Africanized Bee Identification System (FABIS) which was developed by the USDA, Agricultural Research Service, Baton Rouge, La., as a means of quick identification and is based on anatomical dissection and inspection. Collected specimens are identified by their laboratory determined morphological features.

Thus, it will be apparent that there is a need for a reliable field survey technique for distinguishing between different species of honeybees, especially between Africanized and European honeybee species. The need exists for a field-portable instrument which does not require operation by skilled technicians or the physical disturbance of specimens with the associated hazards of attack if Africanized honeybees are present in the surveyed area.

SUMMARY OF THE INVENTION

In view of the above needs, it is an object of this invention to provide a method of identifying different species of honeybees based on analyzing the unique acoustical signatures of the species to determine their identity.

Further, it is an object of this invention to provide a method of identifying different species of honeybees based on detecting their distinct fundamental in-flight wingbeat frequency.

Yet another object of this invention is to provide a method for distinguishing Africanized honeybees from European honeybees by analyzing the acoustical signal produced by the bees in flight to detect the presence of specific frequencies in different known frequency bands indicative of their identity.

Still another object of this invention is to provide a means for carrying out the method of the above objects.

Further, it is an object of this invention to provide a detector for distinguishing between Africanized and European honeybees by means of analyzing their in-flight acoustical signature to detect the presence of specific frequencies herein unique to their identity.

Other objects and many of the attendant advantages will be apparent to those skilled in the art from the following detailed description of the invention taken in conjunction with the drawings.

Briefly, in accordance with the method aspect of this invention, a method is provided for identifying at least two species of flying honeybees that produce different acoustical spectra unique to each species which includes the steps of detecting the acoustical signal produced by the species to be identified and analyzing the acoustical signal to detect the presence of specific known frequencies unique to the identity of the species.

A further aspect of the method of this invention is to provide a method for distinguishing between European and Africanized honeybees which produce acoustical signals in flight that have been found to include power peaks at different frequencies in the ranges of about 210 to 240 Hz and about 260 to 290 Hz, respectively, including the steps of detecting the acoustical signal produced by the bees and analyzing the acoustical signal to detect acoustical signal power peaks in the specified frequency ranges as an indication of the identity of the species.

Further, in accordance with the aspect of providing a means for carrying out the method of this invention, there is provided a device for distinguishing between different species of honeybees which produce different acoustical signal signatures in flight. The device includes an acoustical signal detecting means for detecting the acoustical signal produced by the species to be identified and means for analyzing the detected signal to determine the presence of specific known frequencies therein unique to the identity of the specific one of the species.

In accordance with one embodiment of this invention for identifying either European or Africanized honeybees which produce distinct acoustical signals containing frequencies in the ranges of about 210 to 240 Hz and about 260 to 290 Hz, respectively, the acoustic signal is detected by a microphone positioned to detect the acoustic signal generated by the species to be identified and separate bandpass filters tuned to the distinct frequency ranges are used as the frequency analyzing means to isolate the unique identifying frequencies and the results are indicated by separate indicating means.

In another embodiment, a plurality of tone decoders are employed as the frequency analyzing means to separately detect the distinct frequencies unique to the species identity.

BRIEF DESCRIPTION OF THE DRAWINGS

FIG. 6 is a schematic block diagram of an alternate embodiment of a honeybee identification device according to the present invention which employs tone decoders as the frequency analyzing means to isolate the unique identifying frequencies.

FIG. 7 is a detailed circuit diagram of the structure of one of the tone decoders shown in block form in FIG. 6.

DETAILED DESCRIPTION

As pointed out above, it has been found that the aggressive Africanized honeybees produce distinctly different acoustical signals in flight than that of the European honeybees. Investigations have shown that the center frequencies of the characteristic peaks in the acoustical signatures of flying honeybees are different among subspecies. A collected data base of recordings of acoustical signals from both European and Africanized species of honeybees was analyzed. The recordings of Africanized honeybees were obtained from hives located in Venezuela. Existing technology, such as that used in noise analysis in nuclear power plants to record and monitor fluctuations in process instrumentation, was initially used for recording and analyzing the acoustical signal spectra of these bees. Analysis of the collected data began with standard Fourier analysis of time averaged acoustical signals produced by both species. The resulting series of frequency response plots were then compared to identify common characteristics and acoustic signatures for each of the species were defined. Comparative assessments between signatures of the two species were made to identify distinguishing differences.

Figure 1:
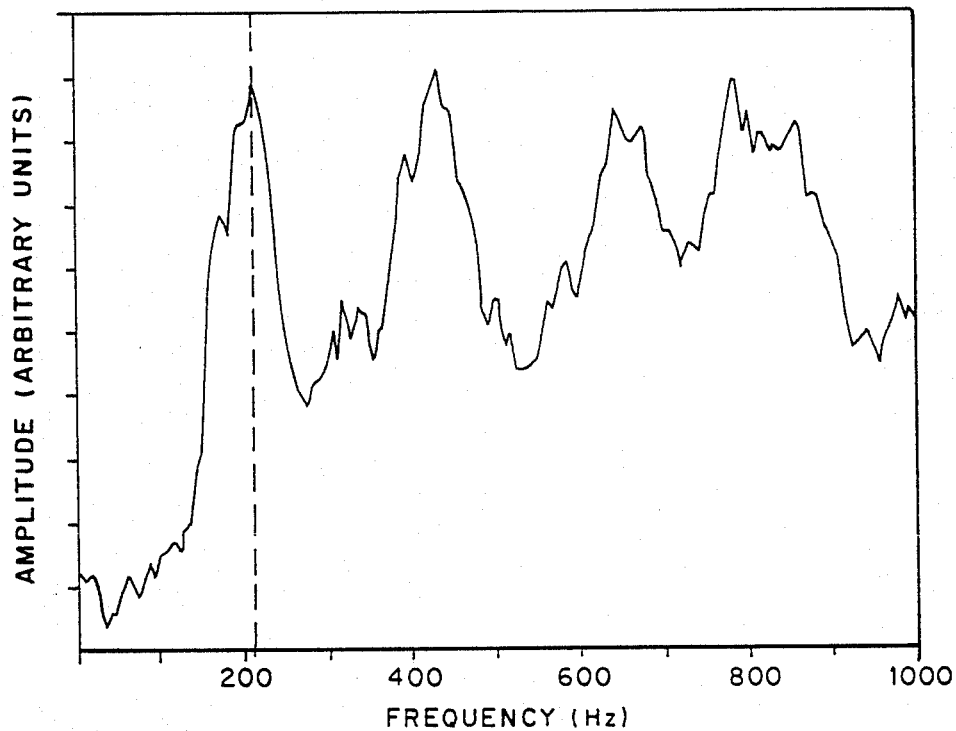
FIG. 1 is a graph of a typical acoustic noise spectrum for a single European honeybee over a frequency range of from 0 to 1,000 Hz
Figure 2:
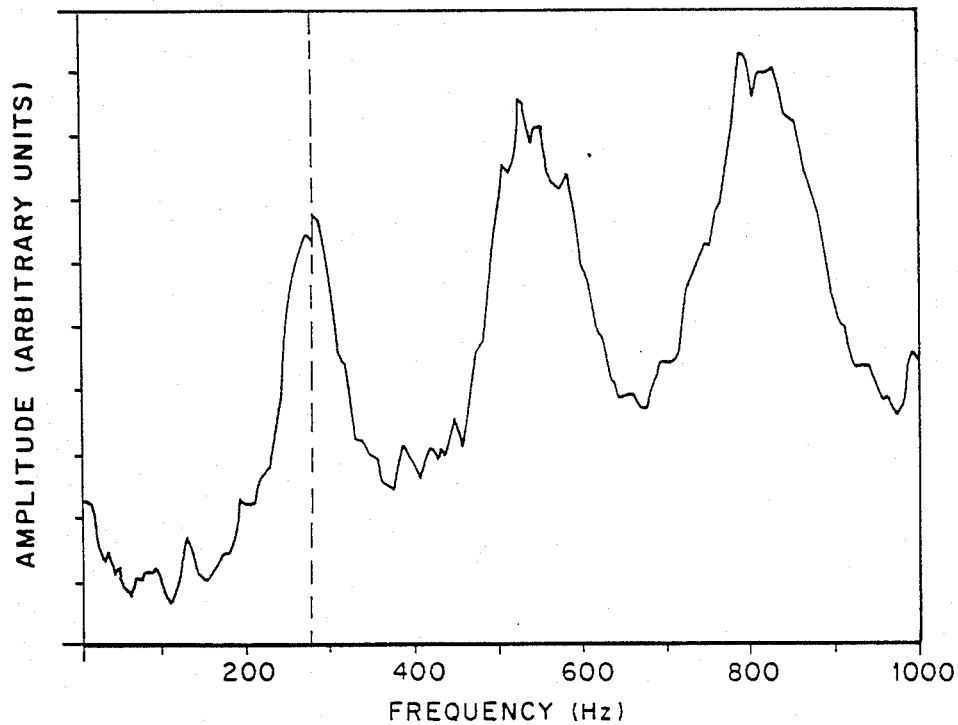
FIG. 2 is a graph of a typical acoustic noise spectrum for a single Africanized honeybee over the same frequency range as in FIG. 1.

The analysis for the worker honeybee acoustical data base did reveal distinguishing differences between the acoustical signatures of flying European and Africanized honeybees. Examples of the acoustical signatures of each of these species are shown in FIGS. 1 and 2. As illustrated by these figures, the flying European honeybee signature has a fundamental power peak in the 210 to 240 Hz range whereas the flying Africanized honeybee signature has a fundamental power peak in the 260 to 290 Hz range. This discovery of a substantial difference in wingbeat frequencies of these two species under similar flight conditions provides the basis for the method of this invention as well as the device for carrying out the method.

Figure 3:
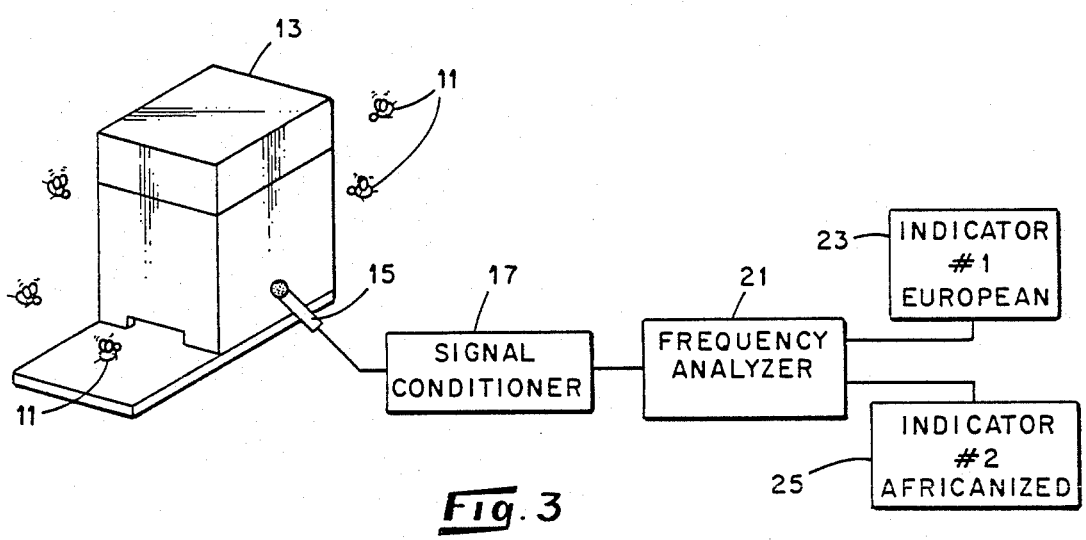
FIG. 3 is a schematic illustration of one application of the method of identifying honeybees according to the present invention.
Figure 4:
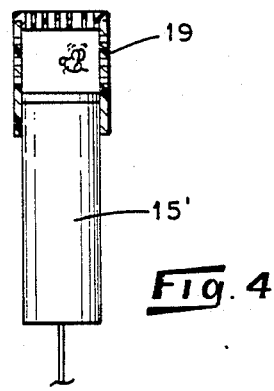
FIG. 4 illustrates an alternate method of detecting the acoustic signal of a single honeybee to be identified.

Turning now to FIG. 3, there is shown an illustration of the method according to the present invention for detecting the presence of either European or Africanized honeybees 11 in or around a conventional honeybee hive 13. It will be understood that the method is not limited to use in areas where the honeybees are concentrated, but may also be used to survey open areas as well. The detector system includes a microphone 15, which preferably has a stable audio frequency response in the range of from 100–500 Hz, which is connected to a signal conditioner circuit 17. The microphone 15 may take various forms such as a directional parabolic type (not shown) which may be used to survey the hive from a distance or to survey areas of foraging honeybees for the purpose of detecting the type of bees present or may be a simple audio frequency microphone which is available in many types. The microphone could be worn by persons approaching a hive or area to be monitored or may be a hand-held model as shown in FIG. 3. Alternatively, the microphone may be attached to an isolation compartment 19, as shown in FIG. 4, which consists of a well ventilated enclosure for the sensing end of a microphone 15' so that the wingbeat frequency of individual captured bees may be detected to ensure that the sounds detected are generated by the isolated bee while filtering out background noise and preventing the bee from escaping.

Once the detected signal is properly conditioned, it is fed to the input of a frequency analyzer 21 which consists of at least two processing channels centered about the two distinct wingbeat frequencies of the European and Africanized bees. If the detected acoustical signal has a relatively large frequency component which falls into the lower range, an output signal is generated at a first output which is connected to a first indicator 23 indicating that the bee is of the European type. However, if the signal has a higher proportionate frequency content in the higher frequency range, an output signal is generated at a second output which is connected to a second indicator 25 indicating that the bee is of the Africanized type. The individual components of the detector for carrying out this method of identification of honeybee species may take various forms as will be apparent from the following description of various embodiments of the detector for carrying out the method according to the present invention. It will be appreciated that in each of the embodiments the basic requirement is to analyze the acoustic signal generated by the flying honeybees in a manner to separately detect the characteristic known wingbeat frequencies for the purpose of separately identifying the species of the bee, or bees. Although only the separate identification of the European or Africanized honeybee types, or both in the case of surveying an area containing both types of bees, has been documented and illustrated herein, the invention may also be applicable for the identification of other species or partially Africanized species which have been found to produce wingbeat frequencies in ranges between that of the European and fully Africanized honeybees.

Figure 5:
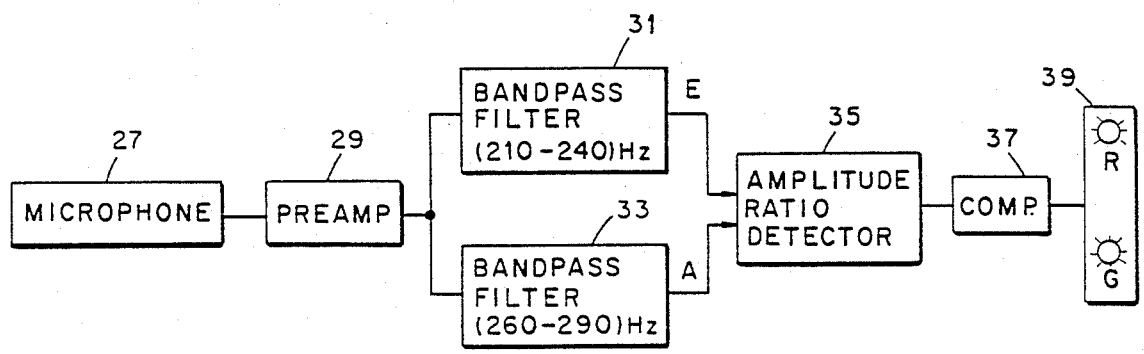
FIG. 5 is a schematic block diagram of one embodiment of a device for identifying different species of honeybees according to the present invention in which bandpass filters are used as the frequency analyzing means to isolate the unique identifying frequencies.

Referring now to FIG. 5, there is shown one embodiment of the detector which uses bandpass filters for he separate detection of the identifying frequencies. A microphone 27 is connected to the input of a preamplifier 29 whose output is commonly connected to separate inputs of bandpass filters 31 and 33. Filter 31 is tuned to pass the detected signal frequency content (E) in the range of from about 210 to 240 Hz, corresponding to the European bee's peak fundamental wingbeat frequency range, while filter 33 is tuned to pass the signal frequency content (A) in the range of from about 260 to 290 Hz, corresponding to the Africanized bee's peak fundamental wingbeat frequency. The outputs of filters 31 and 33 are connected respectively to separate inputs of a signal amplitude ratio detector 35 which generates a signal at the output thereof having an amplitude proportional to the ratio of the two signals. This signal is fed to the input of a comparator 37 which has a selected reference threshold corresponding to the signal level output of the ratio detector which represents a detected ratio of one. When the ratio signal is above the threshold, indicating that the signal A is substantially larger than E, the output of the comparator is switched from a first state to a second state, indicating the presence of Africanized bees. This change in state of the output of comparator 37 may be indicated by connecting the output of the comparator to an indicator device 39 containing a green lamp which is turned on when the output of the comparator is in the first state and a red lamp which is turned on when the comparator switches states, indicating the detection of Africanized bees. This device may be easily incorporated into an inexpensive, portable, battery-operated detector for detecting the presence of Africanized bees in remote field applications.

In field applications where more comprehensive surveys of bee yards or foraging areas are required, an alternate embodiment of the detector of this invention shown in FIG. 6 is provided which not only indicates the presence of either European or Africanized bees, but provides further analysis of the acoustical signals which may be used to detect partially Africanized honeybee species with wingbeat frequencies in ranges between the European and fully Africanized bees. As shown in FIG. 6, a microphone 41 is connected to the input of a bandpass filter 43 which is tuned to pass the frequency content of the sensed acoustical signal in the range of from about 100 to 500 Hz, the acoustic signal range of interest. This filter eliminates extraneous noise signals which may interfere with the analysis of the proper frequencies of interest which fall within the bandpass of the filter. The output of filter 43 is connected to the input of a conventional automatic gain control circuit 45 having a variable gain control level selector 47 which is used to select the gain control level in a conventional manner.

Frequency analysis in this embodiment is provided by a plurality of tone decoders 49 through 57 whose outputs are connected, respectively, to the cathodes of a corresponding plurality of light emitting diodes (LED's) 59 through 67 whose anodes are connected in common to a positive voltage power supply (+V). Each tone decoder circuit (TD 1-5), as illustrated in FIG. 7 for TD 1, is of identical design, but are individually tuned to detect different frequency components of the detected acoustical signal generated by the bees being monitored. As shown in FIG. 7, an integrated circuit tone decoder 69, such as the model LM567C available from National Semiconductor Corp., Santa Clara, Calif., is connected in a conventional manner and includes an externally connected variable resistance RC circuit 71 connected between pins 5 and 6 thereof to vary the RC time constant of an internal local oscillator circuit to select the TD center frequency of response. When the selected frequency for the TD is present in the input signal applied to pin 3, ground potential is applied to pin 8 which turns on the corresponding LED, in this case LED 59', connected to output pin 8. These tone decoders are amplitude sensitive in that the extent of the frequency band of detection about the center frequency increases as the amplitude of the signal applied to the input increases. Therefore, the percent bandwidths of the TDs 49-57 are controlled by the selected AGC 45 control level which is selected as described above. Therefore, the AGC level control knob may be mounted on the front panel of the detector and indicated as a % bandwidth control option if desired.

In either case, the center frequency of each TD 49-57 is selected to detect the various frequencies of interest as indicated in FIG. 6. Since the European bees emit wingbeat frequencies in the range of from about 210 to 240 Hz and the Africanized bees emit wingbeat frequencies in the range of from about 260 to 290 Hz, a plurality of TDs may be used, as shown in FIG. 6, to completely cover the ranges and also provide information which may be useful for identifying partially Africanized swarms of honeybees from which it has been observed that the wingbeat frequencies are in the mid range of frequencies between these two ranges. Therefore, there are preferably five tone detectors (TD 1-5) with center frequencies of 210, 226, 242, 261, and 280 Hz, respectively. The TDs 1 and 2 cover the range of frequencies for European honeybees between 220 and 240 Hz and thus activate green LEDs 59 and 61 accordingly. TD 3, which is set at 242 Hz, is connected to an amber LED 63 which indicates the detection of frequencies in the range which may be produced by partially Africanized bees. TDs 4 and 5 cover the range of frequencies for Africanized bees between about 260 and 290 Hz and thus activate red LEDs 65 and 67 when frequencies in this range are detected.

This detector may also be provided in the form of a portable detector with a front panel containing the percent bandwidth adjustment feature together with the LEDs 59 through 67. By providing the adjustable percent bandwidth tone detection feature and the separate LED readouts, more selective surveys of areas or hives suspected of containing fully or partially Africanized honeybees may be made.

Figure 8:
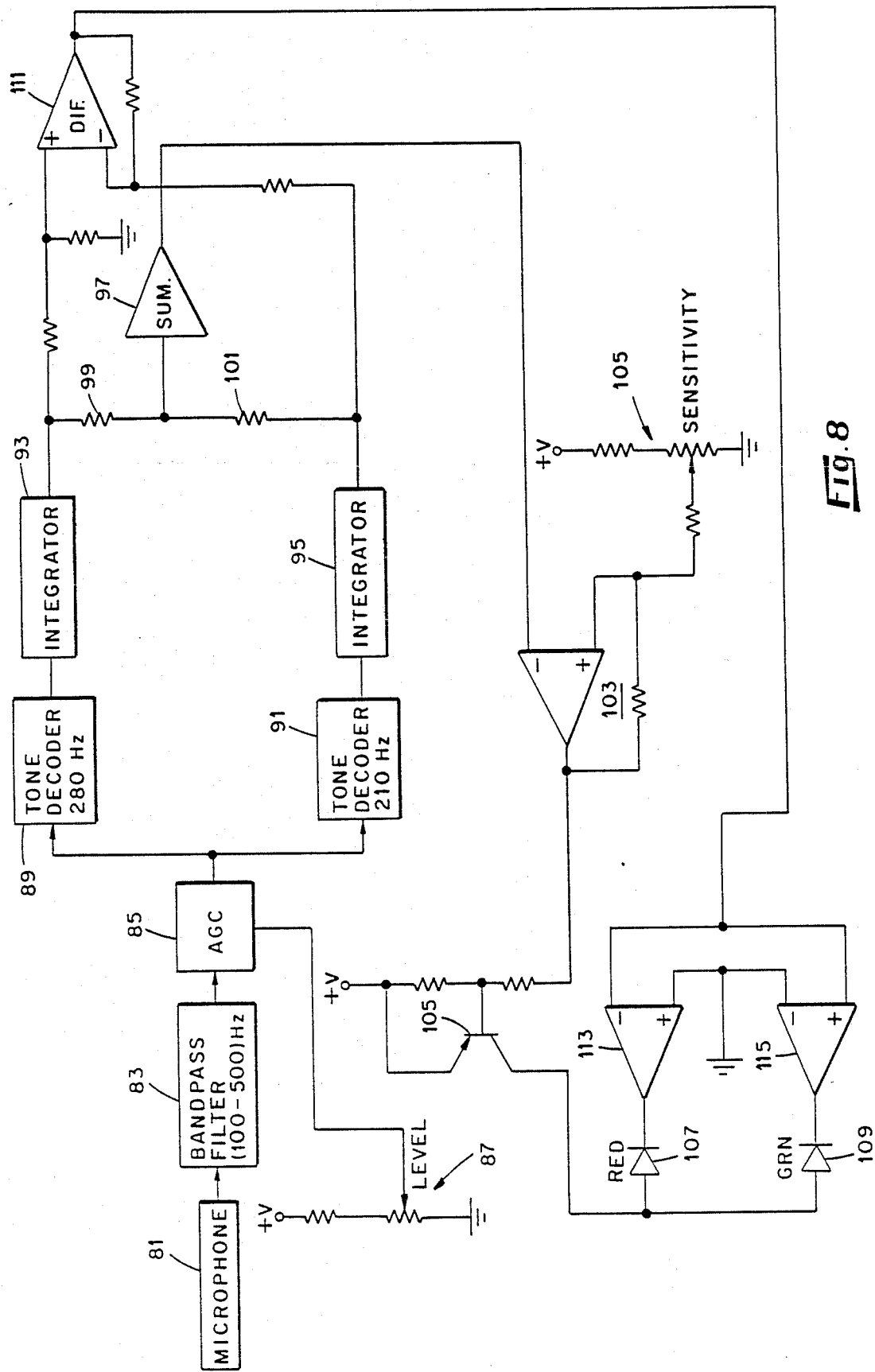
FIG. 8 is a schematic diagram of a further embodiment of a honeybee identification device of the tone decoder type made in accordance with the present invention.

Referring now to FIG. 8, there is shown another embodiment of a detector according to the invention which includes additional features, some of which may also be included in the embodiments above. In this embodiment, the microphone 81 is connected to a bandpass filter 83 whose output is connected to an AGC 85 with a gain level adjusting circuit 87 in the same manner as in the embodiment shown in FIG. 6. The output of the AGC 85 is connected in common to the inputs of two tone decoders 89 and 91, which are identical in structure to that shown in FIG. 7, with the LED at the output pin 8 removed and the +5 V supply connected through the resistor shown to pin 8. With the TD connected in this manner, pulses are produced at the pin 8 output each time the TD detects the appropriate frequency in the applied signal. TD 89 is set with a center frequency of 280 Hz to detect wingbeat frequencies characteristic of Africanized bees while TD 91 is set with a center frequency of 210 Hz to detect wingbeat frequencies characteristic of European bees. The outputs of TDs 89 and 91 are connected, respectively, to the inputs of pulse integrators 93 and 95. These integrators are identical and have an integrating time constant of about 2 seconds. The purpose of the pulse integrators is to eliminate the constant flickering of the indicator LEDs which may be prevalent in the embodiment of FIG. 6 due to erratic wing motion particularly when the single bee chamber 19 (FIG. 4) is employed. Thus, by integrating the pulses these problems are eliminated in the output indicators.

The outputs of integrators 93 and 95 are connected to the input of a summing amplifier 97 through load resistors 99 and 101, respectively. The output of amplifier 97 is connected to the input of a comparator circuit 103. The comparator circuit 103 includes a variable reference set point selector circuit 105 which allows the operator to vary the detector sensitivity by adjusting the reference set point to the comparator 103. The output of the comparator 103 is connected to the base of a switching transistor 105 which is connected in the conducting path of the +V power supply to the anodes of indicator LEDs 107 and 109. By summing the output levels of the integrators 93 and 95 by means of the summing amplifier 97 and applying this signal to the input of comparator 103, the integrated outputs from either or both TDs 89 and 91 must exceed the reference level set for the comparator 103 to enable the LEDs 107 and 109 to be activated. Thus, the sensitivity of the detector is selected by the appropriate setting of a potentiometer in the selector circuit 105. This feature may be used to eliminate false indications when the signal levels are too low to allow for accurate identification.

To activate the appropriate indicator LED the outputs of the integrators 93 and 95 are connected to separate inputs of a differential amplifier 111. The output of integrator 93 is connected to the noninverting input (+) of amplifier 111 and the output of integrator 95 is connected to the inverting (−) input of amplifier 111. Therefore, if the output of integrator 93 is greater in amplitude than that of integrator 95 which indicates that the detected signal is predominantly in the 280 Hz range, the output of amplifier 111 is positive otherwise the output of amplifier 111 will be negative, indicating that the output of integrator 95 is greater and indicating that the detected signal is predominantly in the 210 Hz range. Thus, the output of amplifier 111 is connected in common to the inputs of comparators 113 and 115 whose outputs are connected, respectively, to the cathodes of LEDs 107 and 109. The comparators 113 and 115 compare the output of amplifier 111 with reference ground potential to determine if the signal is positive or negative and activates the appropriate LED 107 or 109 accordingly, assuming that sufficient signal is available to activate the enabling switching transistor 105. Thus, it will be seen that if the detected acoustical signal contains a predominant component of energy in the 260–290 Hz range indicating the detection of Africanized bees, the output of amplifier 111 will go positive causing comparator 113 to switch states and turn LED 107 "ON" However, if the predominant component of acoustical energy is in the lower range (210–240 Hz) detected by TD 91, the output of amplifier 111 will be negative, causing comparator 115 to switch states and turn LED 109 "ON", indicating the presence of European honeybees.

Thus, it will be seen that a simple method and device for identifying different species of honeybees based on differences in their in-flight acoustical signatures have been provided which may be readily implemented by non-technical personnel for quickly surveying honeybee swarms or areas containing foraging bees to determine their species identity. Although the invention has been described in conjunction with preferred embodiments, it will be apparent to those skilled in the art that various modifications and changes may be made therein without departing from the spirit and scope of the invention as set forth in the following claims.

We claim:

1. A method of identifying at least two different species of honeybees whose wing movements produce distinctly different distinguishing frequency bands for each said species within an acoustical signal spectra, comprising the steps of:

detecting said acoustical signal spectra produced by said honeybees to be identified; and analyzing said detected acoustical signal spectra simultaneously with at least two frequency responsive circuits, one of said circuits responsive to a frequency band of one of said species and a second of said circuits responsive to a frequency band of a second of said species, to determine the presence of said distinguishing frequency bands specific to the identity of a particular species as an indication of the species of said honeybees being identified.

2. The method as set forth in claim 1 wherein said different species of honeybees includes European and Africanized species whose wing-movement acoustical signal spectra contain distinct frequencies in corresponding first and second frequency ranges of from about 210 to 240 Hz and from about 260 to 290 Hz, respectively, and wherein said analyzing step includes analyzing the frequency content of said detected acoustical signal spectra to detect the presence of frequencies within said first and second frequency ranges as separate indications of the identity of said honeybees as of the European or Africanized species.

3. The method as set forth in claim 2 wherein said detecting step includes detecting the in-flight acoustic signal spectra generated by said species of honeybees to be identified.

4. The method of claim 3 further including the step of isolating a single honeybee specimen, whose species is to be identified, prior to detecting the acoustical signal generated by said isolated specimen 5. A device for identifying at least two different species of honeybees whose wing movements produce distinctly different acoustical signal spectra, each specie of honeybee producing specific and distinct frequency bands in said signal spectra, comprising:

an acoustical signal detecting means for detecting an acoustical signal spectra produced by at least one of said species of honeybees to be identified and generating an electrical signal at an output of said detecting means proportional to said acoustical signal spectra; and an electrical signal frequency responsive means for receiving and analyzing said electrical signal and for generating separate species identification signals in response to specific frequencies in said electrical signal within said frequency bands associated with the identity of a particular honeybee species.

6. The device as set forth in claim 5 wherein said different species of honeybees to be identified include European and Africanized species of honeybees and wherein said specific frequency bands include first and second immediately frequency bands of about 210 to 240 Hz and 260 to 290 Hz, respectively, associated with the identity of European and Africanized honeybee species, respectively.

7. The device as set forth in claim 6 further including indicating means responsive to said separate identification signals for indicating the presence of said identified honeybee species.

8. The device as set forth in claim 6 wherein said acoustic signal detecting means includes a microphone having a stable audio frequency response band in the range of at least 100 to 500 Hz.

9. The device as set forth in claim 8 wherein said electrical signal frequency responsive means includes:
   first and second bandpass filters having frequency bandpass ranges of about 210 to 240 Hz and about 260 to 290 Hz, respectively, said first and second filters each having an input coupled to the output of said microphone and an output;
   a signal amplitude ratio detector means having first and second inputs connected respectively to outputs of said first and second bandpass filters for generating an output signal proportional to the ratio of signals applied to said first and second inputs thereof;
   a comparator means for comparing the amplitude of the output signal of said ratio detector means with a reference voltage level and providing an output signal which changes states when the output of said ratio detector means exceeds said reference threshold; and
   an indicator means responsive to the output of said comparator for indicating the identity of the honeybee species in accordance with the state of the signal output of said comparator.

10. The device set forth in claim 8 wherein said electrical signal frequency responsive means includes:
    a plurality of N tone decoders where N is the total number of said tone decoders, each decoder having an input coupled to the output of said microphone and each decoder tuned to be activated by the detection of different frequencies in ranges from about 200 to 290 Hz in selected progressive steps beginning with a first decoder through the Nth one of said decoders, and each decoder generating an output signal at an output thereof when activated; and
    a plurality of indicator lamps corresponding in number to said plurality of N tone decoders connected to respective of said outputs of said plurality of tone decoders so that the identity of said honeybee species is indicated by said indicator lamps associated with said activated tone decoders.

11. The device as set forth in claim 8 wherein said electrical signal frequency responsive means includes:
    first and second tone decoder means for producing output pulses at respective outputs thereof in response to frequencies in said first and second frequency bands respectively associated with said European and Africanized honeybee species;
    first and second pulse integrators, each pulse integrator having an input and an output, said inputs being connected respectively to said outputs of said first and second ton decoder means for integrating said output pulses of said respective tone decoder means and providing time averaged signals at respective outputs of said integrators proportional to said output pulses of said first and second tone detector means;
    a summing amplifier means connected to said outputs of said first and second pulse integrators for generating an output signal at an output thereof proportional to the sum of said outputs of said integrators;
    a difference amplifier means responsive to said outputs of said integrators for producing a switching signal at an output of said difference amplifier means which is switched to a first state when said signal at said output of said first integrator exceeds said signal at said output of said second integrator, and to a second state when said signal at said output of said second integrator exceeds said signal at said output of said first integrator; and
    an indicator means including first and second indicating lamps which are separately activated in response to said output states of said difference amplifier means and having an enabling input responsive to a preselected output level of said summing amplifier means to enable activation of said first and second indicator lamps in response to said output states of said difference amplifier means so that when the first one of said lamps is activated due to said difference amplifier means being in said first state of identification of European honeybees is indicate, and when a second one of said lamps is activated due to said difference amplifier means being in said second state the identification of Africanized honeybees is indicated.

12. A method of identifying different species of honeybees, each of said species having wing movements that produce detectable acoustical signal spectra with different specific distinguishing frequency bands, which comprises:
    detecting said acoustical signal spectra of said species to be identified and producing an electrical signal corresponding to said spectra;
    feeding said electrical signal corresponding to said spectra simultaneously into at least two frequency responsive circuits, said two frequency responsive circuits adapted to produce an output signal in response to individual of said different specific distinguishing frequency bands of said species; and
    determining the presence of said output signal from said frequency responsive circuits as a measure of the identity of said species of honeybees corresponding to the specific distinguishing frequency band of said frequency responsive circuits.

13. A field survey device for identifying species of honeybees whose wing movements produce uniquely different distinguishing frequency bands in an acoustical signal spectra in a range of about 200 to about 290 Hz, which comprises:
    an acoustical detecting means for detecting an acoustical signal spectra produced by said species of honeybees to be identified and for generating an electrical signal at an output thereof proportional to said acoustical signal spectra;
    a plurality of tone decoders designated from a first decoder to a Nth decoder, for receiving said electrical signal proportional to said acoustical signal spectra, each of said decoders tune to be activated by the detection of different assigned frequencies in ranges from about 200 to about 290 Hz in selected progressive steps beginning with said first decoder through said Nth decoder, with each of said decoders providing an output signal when activated by said assigned frequency in said acoustical signal spectra electrical signal; and
a plurality of indicator means, each of said indicator means connected to one of said plurality of decoders, whereby on output signal of a decoder activates said indicator means associated therewith to identify the presence of a species of honeybee corresponding to said assigned frequency of said activated decoder.

* * * * *